United States Patent
Johnson

(10) Patent No.: US 11,330,778 B2
(45) Date of Patent: May 17, 2022

(54) CANNABIS PLANT NAMED 'FS-TP2'

(71) Applicant: Jordan Randall Johnson, Mariposa, CA (US)

(72) Inventor: Jordan Randall Johnson, Mariposa, CA (US)

( * ) Notice: Subject to any disclaimer, the term of this patent is extended or adjusted under 35 U.S.C. 154(b) by 0 days.

(21) Appl. No.: 16/903,853

(22) Filed: Jun. 17, 2020

(65) Prior Publication Data
US 2020/0315118 A1    Oct. 8, 2020

Related U.S. Application Data

(63) Continuation of application No. 16/820,144, filed on Mar. 16, 2020.

(60) Provisional application No. 62/831,101, filed on Apr. 8, 2019, provisional application No. 62/819,586, filed on Mar. 16, 2019.

(51) Int. Cl.
    *A01H 5/12*          (2018.01)
    *A01H 6/28*          (2018.01)

(52) U.S. Cl.
    CPC ................ *A01H 6/28* (2018.05); *A01H 5/12* (2013.01)

(58) Field of Classification Search
    CPC ..................................... A01H 6/28; A01H 5/12
    See application file for complete search history.

(56) References Cited

PUBLICATIONS

Dutch Passion Frisian Duck; Web Blog, 8 pages; https://dutch-passion.com/en/blog/dutch-passion-frisian-duck-cannabis-like-you-have-never-seen-before-n674. (2015) (Year: 2015).*
Growing Marijuana Perfectly Nov. 2019 pp. 1-6; Freakshow: Growing Marijuana that Doesn't Look Like Marijuana http//growingmarijuanaperfectly.com/2019/10/22/freakshow-growing-marijuana-that-doesn't-look-like-marijauna/ (Year: 2019).*
Dutch Passion Frisian Duck: Web Blog; 8 pages (2015) https://dutch-passion.com/en/blog/dutch-passion-frisian-duck-cannabis-like-you-have-never-seen-before-n674. (Year: 2015).*

* cited by examiner

*Primary Examiner* — Russell Kallis
(74) *Attorney, Agent, or Firm* — Plant & Planet Law Firm; Dale C. Hunt; Richard A. Ryan

(57) ABSTRACT

The unique annual herbaceous *Cannabis* plant variety 'FS-tp2' is provided. The variety is a selection resulting from cross of female parent *Cannabis sativa*. hybrid 'Pineapple Express' and male parent *Cannabis sativa* hybrid 'Holy Banana'. Selective breeding was used to obtain the desired morphological features described. The morphological features that allow this variety 'FS-tp2' to be distinguished from other *C. sativa* varieties are its outstanding features such as high leaflet count, with narrow leaves.

8 Claims, 7 Drawing Sheets

CANNABIS PLANT NAMED 'FS-TP2'

CROSS REFERENCE TO RELATED APPLICATIONS

This application is a continuation of U.S. Non-Provisional patent application Ser. No. 16/820,140 filed on Mar. 16, 2020 which in turn claims priority to U.S. Provisional Application No. 62/819,586 filed on Mar. 16, 2019 and U.S. Provisional Application No. 62/831,101 filed on Apr. 8, 2019. The entire contents of each of the foregoing are hereby incorporated by reference herein.

BACKGROUND OF THE INVENTION

Field of the Invention

The present invention relates to a new and distinct annual variety of *C. sativa* hybrid, which has been given the variety denomination of 'FS-tp2' 'FS-tp2' is intended for use as medicinal herb for sale in *cannabis* dispensaries and as a home garden plant.

Background of the Related Art

The genus *Cannabis* has been in use by humans for millennia, due to the multiplicity of its benefits to humans, including the considerable value and utility of its fiber, the nutritional value of its seeds, and the medicinal value of its floral parts and products made from them. Currently the genus is under intense legal commercialization in the United States as industrial hemp for a variety of purposes including biodegradable plastics and building materials, clothing, paper, food, fuel and medicines.

Cannabidiol (CBD) extracted from *Cannabis* is widely used in over-the-counter medicines and topical treatments, and is also the active ingredient in the FDA-approved drug Epidiolex. CBD is just one of at least dozens—perhaps hundreds—of cannabinoids endogenous to *Cannabis*, tetrahydrocannabinol (THC) being the other cannabinoid that is most well-known. The cannabinoids as a group interact with the human endocannabinoid receptors, which are distributed in the brain and throughout the body. The study of the endocannabinoid system (ECS) in humans and other mammals is an area of increasing interest and holds tremendous promise for the future of medicine. See, e.g., Russo (2019). *Cannabis* and Pain, *Pain Medicine,* 20(10): 1093/pm/pnz227; and Russo (2016). Clinical Endocannabinoid Deficiency Reconsidered: Current Research Supports the Theory in Migraine, Fibromyalgia, Irritable Bowel, and Other Treatment-Resistant Syndromes, *Cannabis Cannabinoid Res.* 1(1): 154-165.

Non-hemp forms of *Cannabis*, frequently referred to as marijuana, have been legalized for medicinal use in many states and also for recreational use (sometimes called "adult use") in a growing number of states and including Alaska, California, Colorado, Illinois, Maine, Massachusetts, Nevada, Oregon, Vermont, and Washington, while remaining "fully illegal" in 11 states. It is also now permissible under the law of at least 15 states for individuals to grow their own marijuana plants, although in many of these states the home-grow is limited to some sort of authorized medicinal use. It is expected that the wave of legalization will continue to the point of some form of federal legalization or decriminalization.

Typically, marijuana products are available to users for purchase in specialized "dispensaries" that offer dried flower, edibles, tinctures, extracts, and the like. However, there is a strong interest in the legal home-grow approach to obtaining marijuana products, and seed sales of many different *Cannabis* varieties are robust. To date, little if any work has been done in development of ornamentally unique and attractive, easily-cultivated *Cannabis* plants for in-home growing and use.

SUMMARY OF THE INVENTION

Embodiments of the invention relate to a seed from *Cannabis* plant designated 'FS-tp2' wherein a representative sample of seed of said plant has been deposited under NCIMB No. 43854.

Some embodiments of the invention relate to a *Cannabis* plant, or plant part, tissue, or cell thereof produced by growing the seed from *Cannabis* plant designated 'FS-tp2', or a descendant thereof. In some embodiments, the plant or plant part displays Type 2 leaf morphology, as defined herein.

Some embodiments of the invention relate to the use of the plant in a breeding program to produce *cannabis* progeny comprising at least one of Type-2 leaf morphology and genetic capacity to produce Type-2 leaf morphology in progeny thereof.

Some embodiments of the invention relate to the *Cannabis* plant, or plant part, tissue, or cell comprising at least one of a cannabinoid profile and a terpene profile as set forth in Tables 1 and 2, respectively.

Some embodiments of the invention relate to the *Cannabis* plant part of claim 2, wherein said plant part is selected from the group consisting of: stems, trichomes, leaves, and flower buds.

Some embodiments of the invention relate to a *Cannabis* plant descended from the plant, or plant part, tissue, cell or seed, wherein the plant is a clonal descendent.

BRIEF DESCRIPTION OF THE DRAWINGS

The accompanying photographs show the typical appearance of the new variety 'FS-tp2'.

DETAILED DESCRIPTION

The present invention provides a new and distinct variety of *Cannabis* having unique and highly attractive ornamental features. Leaves of typical *Cannabis* plants are palmately compound (shaped like the open hand, with multiple parts), with from 3 to 13 veined, serrated leaflets like fingers of the open hand. The leaves of FS-tp2 have a structure in which leaflet of the palmately compound leaf have multiple, usually numerous lobes or secondary leaflets. The presence of these numerous secondary leaflets is characteristic of the new and distinct morphology of the leaves of the new variety and is referred to herein as Type-2 leaf morphology. The morphological transition from the typical *Cannabis* leaf to the most distinctive leaves of FS-tp2 appears to follow a transition in which the deep serrations of a typical leaf deepen further to somewhat hooked serrations and further to lobes and ultimately to secondary leaflets. An examination of leaves of various stages of growth and development and at different stages of maturity of the plant shows elements of this transition.

Figure 1:
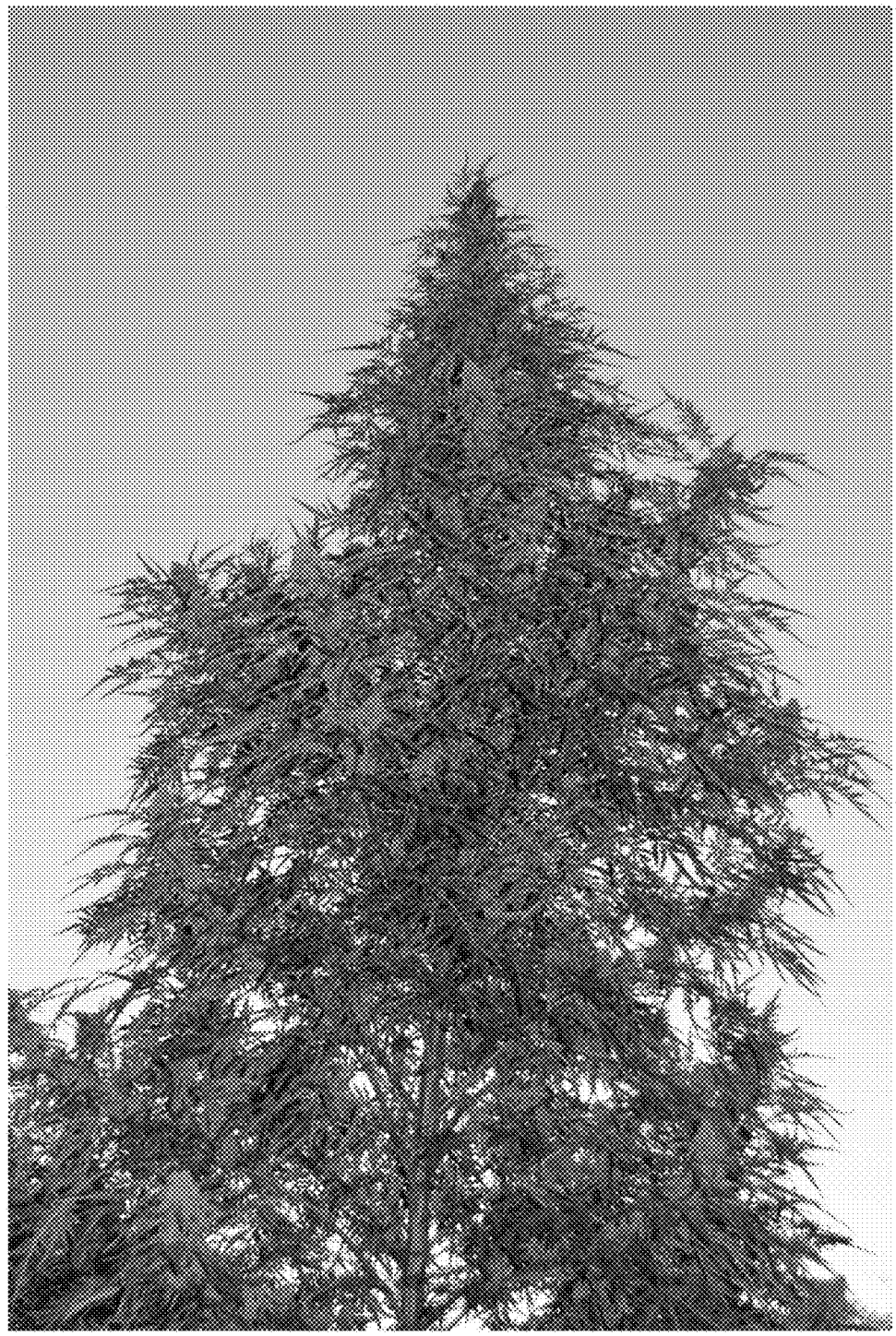
FIG. 1 is a photograph of the new variety 'FS-tp2' showing the entire plant taken from below. The photo demonstrates the structure and foliage of the plant.
Figure 2:
FIG. 2 is a photograph of the fascicle of new variety 'FS-tp2' to demonstrate the Type 2 leaf morphology.
Figure 3:
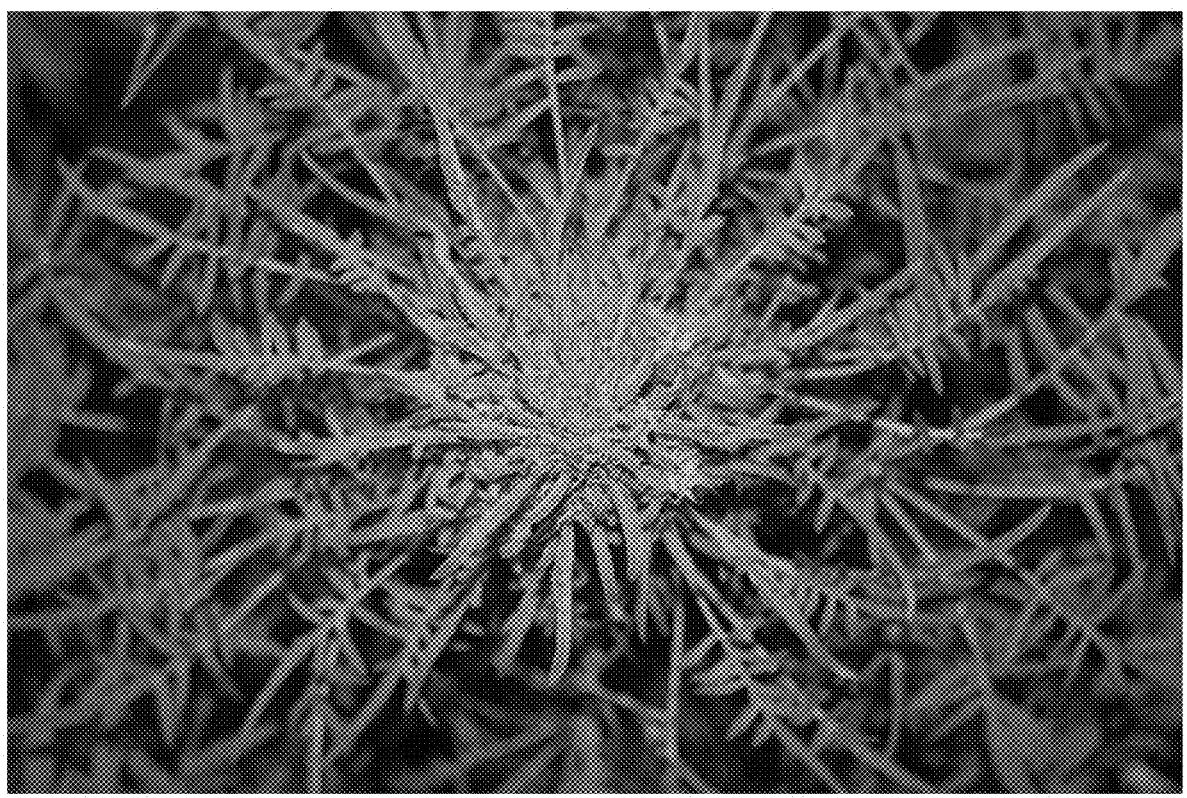
FIG. 3 is a photograph showing the fruit of new variety 'FS-tp2' from above amongst the leaves demonstrating the Type 2 leaf morphology.
Figure 4:
FIG. 4 is a photograph of the new growth shown from above of the new variety 'FS-tp2' exhibiting the Type 2 leaf morphology.
Figure 5:
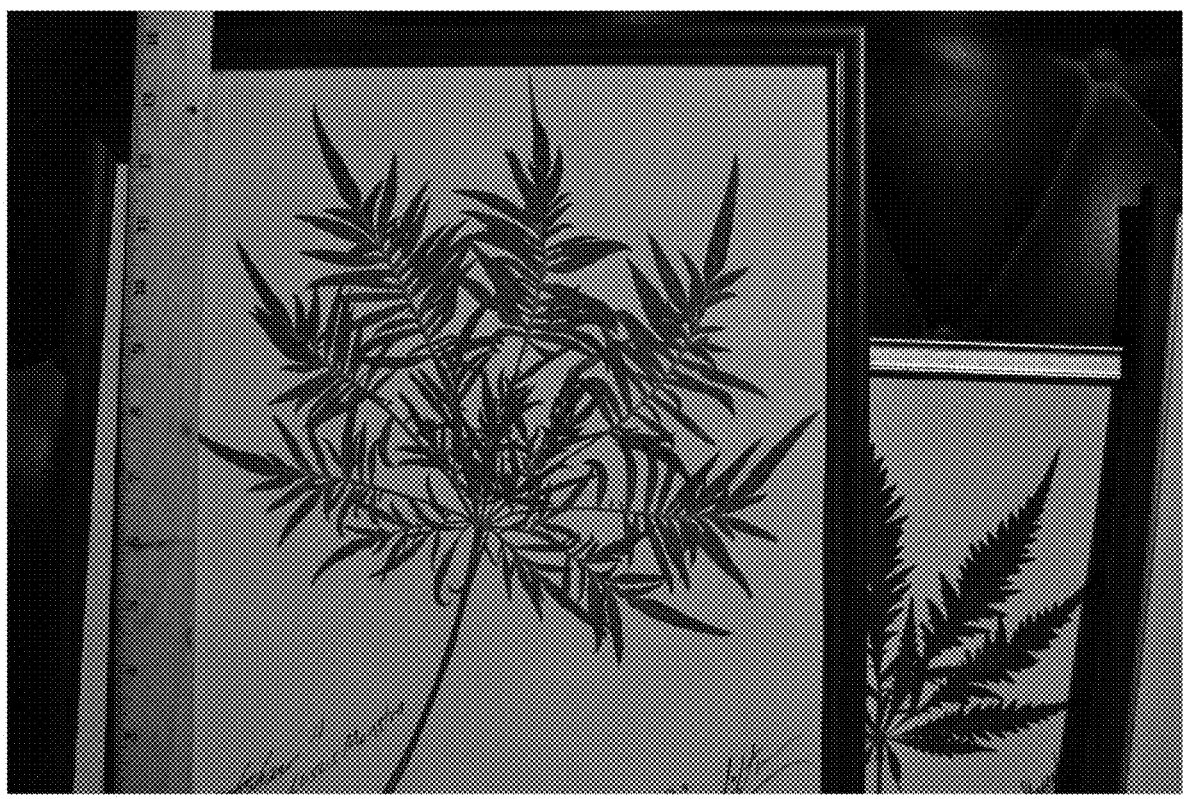
FIG. 5 is a photograph of the fascicle of the new variety 'FS-tp2' demonstrating the Type 2 leaf morphology.
Figure 6:
FIG. 6 is a photograph of a collection of fascicles of the new variety 'FS-tp2' to demonstrate the Type 2 leaf morphology.
Figure 7:
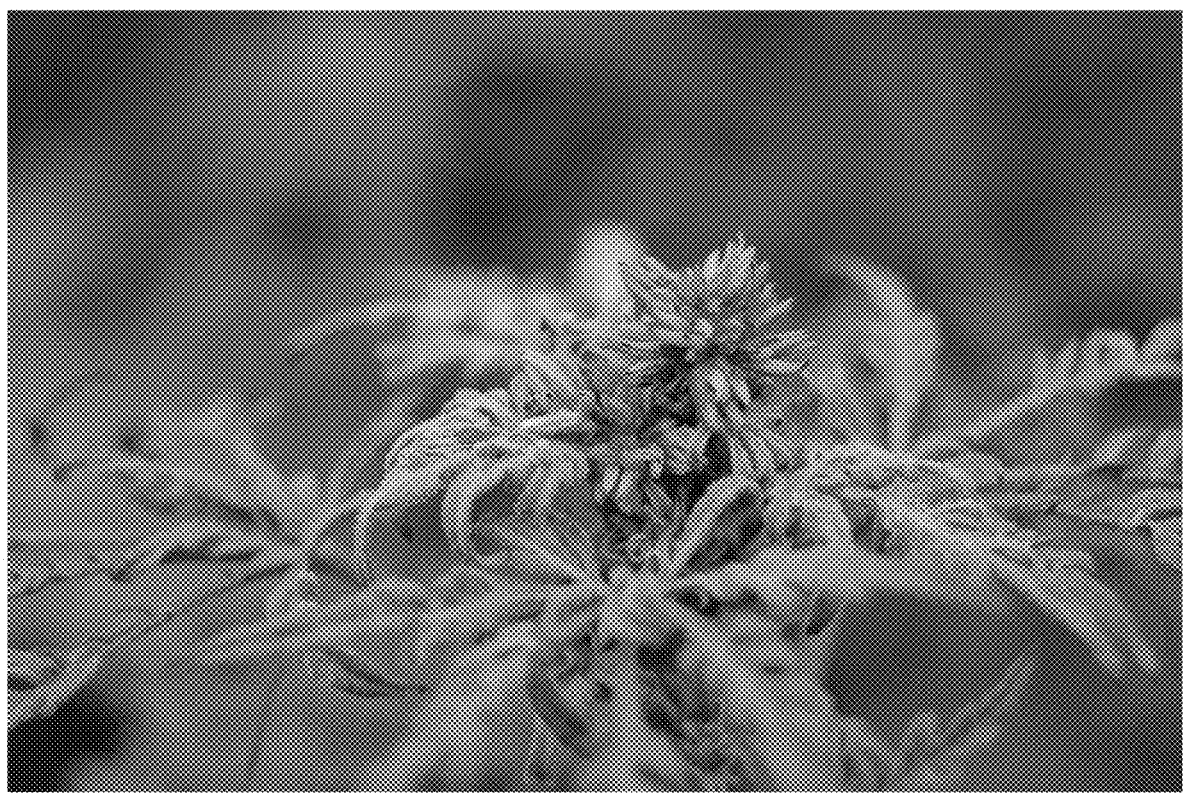
FIG. 7 is a photograph of a male flower of the new variety 'FS-tp2'.

Leaves of the FS-tp2 variety typically have 5-9 leaflets with lengths that vary from the shortest near the outside of the leaf at its base to the longest in the middle (See FIG. 6). Each leaflet has many secondary leaflets ranging in number from 9 or fewer per leaflet to 30 or more per leaflet, in a pattern in which the smaller lateral leaflets closer to base of the leaf have fewer secondary leaflets and the longer leaflets toward the middle of the leaf have more secondary leaflets. In early leaves, some of the leaflets show less of the secondary leaflet morphology, such that part of the leaflet is substantially intact while lower portions of the leaflet are lobed into secondary leaflets. This combination of multiple leaflets and numerous secondary leaflets creates the characteristic, highly unusual fern-like appearance of individual leaves and an also highly unusual "bushy" or "fuzzy" appearance of the plant as a whole.

The new *C. sativa* hybrid variety is a selection resulting from cross of a female parent *C. sativa* hybrid variety 'Pineapple Express' (unpatented) and a male parent *C. sativa* hybrid variety 'Holy Banana' (unpatented) in eastern Madera County, California, U.S.A during 2017. The new phenotype was found in the F1 progeny as a male with pronounced morphological features including a larger than normal number of leaflets, narrow leaves, and deep hooked serrations on the leaves. The male was crossed to an F1 female with less pronounced morphological features in 2017. The seedlings of the F2 generation were screened in 2018 and from a total of 300 seedlings, 30 were found that exhibited the desired morphological features of large number of secondary leaflets on the leaflets. A single male and 5 females of the F2 progeny were selected for breeding to create the F3 generation in 2018. The F3 progeny were 100% found to exhibit the selected morphology of large numbers of secondary leaflets on the leaflets.

The selection has been propagated in eastern Madera County, Calif., U.S.A. Sexual reproduction of the new variety by cross of F3 progeny since 2018 at Madera County, Calif., U.S.A. has demonstrated that the new variety reproduces true to type with all of the characteristics, as herein described, firmly fixed.

The new *C. sativa* hybrid variety is a selection resulting from cross of *C. sativa* hybrid 'Pineapple Express' (unpatented) and *C. sativa* hybrid 'Holy Banana' (unpatented) in Madera County, Calif., U.S.A. The female parent *C. sativa* hybrid 'Pineapple Express' is a cross of *C. sativa*. ssp: indica and *C. sativa* ssp: *sativa* that is an "indica-dominant" type. The male parent is a *C. sativa* hybrid 'Holy Banana' that is also an indica-dominant type. The male parent was derived from a cross of *C. sativa* hybrid 'Big Sur Holy Weed' (unpatented) and *C. sativa* hybrid 'Banana Kush' (unpatented).

'FS-tp2' has several morphological differences from parent lines. The first is possession of bipinnate leaflets, rather than the characteristic deeply lobed leaves of the species. The parents both display simple palmate lobed leaves, while in FS-tp2 although the venation remains unaltered, the leaflet shape is bipinnate, with secondary leaflets along both sides of each vein. The number of veins and secondary leaflets increases with the age of the plant and associated typical changes in leaf morphology. The plant growth is unaltered.

The new *cannabis* variety was designated 'FS-tp2' and has been planted since 2018.

The new *C. sativa* hybrid variety is a selection resulting from cross of *C. sativa* hybrid 'Pineapple Express' and *C. sativa* hybrid 'Holy Banana' in Madera County, Calif., U.S.A. In the F1 progeny 2 males of the 20 plants exhibited anomalous morphologies referred to as 'Type 2' morphology. Type 2 morphology can be defined as having a palmate leaf structure with typically 5 to 9 leaflets featuring numerous (usually about 9 to 30 or more) bipinnate lobes or secondary leaflets, and/or the any of the unique features depicted in the photographs. In general and colloquial terminology, Type 2 morphology can refer to a *Cannabis* leaf having an atypical, fern-like morphology.

In further crosses, the male with more pronounced Type 2 morphology was used to pollinate a female F1 that exhibited subtle, but similar, Type 2 morphology to generate the F2 progeny. 300 seed-starts of the F2 generation were screened for the desired Type 2 morphological features. 30 F2 plants were identified that exhibited the increased number of leaflets. Light deprivation was used to induce flowering and pollination as desired with a single male F2 plant to pollinate 5 female F2 plants to produce the F3 generation ('FS-tp2') and the remainder of the F2 generation were destroyed. The F3 seeds were harvested and chilled to allow subsequent small scale (n=9) screening. 100% of the F3 generation were found to express the Type 2 morphology of increased leaflets. All crosses and screenings were performed in Madera County, Calif., U.S.A.

The selection has undergone propagation in eastern Madera County, Calif., U.S.A. Sexual reproduction of the new variety by cross of F3 progeny since 2018 at Madera County, Calif., U.S.A. has demonstrated that the new variety reproduces true to type with the characteristics, as herein described, firmly fixed.

The selection is of tropical, sub-tropical, narrow-leaf drug (NLD) *C. indica* ssp. indica, with the THC allele Bt, predominately, and also contains approximately 25% broad-leaf drug (BLD) *C. indica* ssp. *afghanica* also with THC allele Bt. NLD and BLD biotypes of *Cannabis* and their ancestor biotypes, are discussed at length in Clarke, R. C. and Merlin, M. D. (2013) et al, *Cannabis: Evolution and ethnobotany*. University of California Press.

There are at least five features which make this variety of *Cannabis* unusual and novel:

1. Type 2 morphology.
2. Hyper-plasticity (environmental plasticity). Hyper-plasticity provides a heightened ability to express new and different morphologies, presumed to occur due to gene recombination, and also the unique ability to express altered morphologies according to various changes in environmental conditions. Because of this, many anatomical manifestations may be observed as indicia of hyper-plasticity. This trait of being a changeling, or shapeshifter, is a novel characteristic in *Cannabis* plants.
3. Male flowers typically lack staminate calyxes (petals). They also have no filament, but produce profusions of stamens which are of an unusually tight density for a natural staminate *Cannabis* plant.

4. Seed Morphology. The seeds are paler in color (at total ripeness and maturity) than common *Cannabis* plants. The seeds also have prominent venation on outer shell surface, and are more intricately arranged inside.

5. This variety often has the appearance of multiple cotyledons, although these may be manifestations of some sort of "leafleting" in the cotyledons. Observations of seedlings have shown what appear to be 3 or 4 and up to 6 cotyledons. The first true leaves are typically not singular, but are usually of a 3 or 5 leaflet configuration. The first few sets of leaves typically exhibit palmate, compound pinnate configuration, and the complexity increases, as do the number of leaflets and sub-leaflets, as the subsequent leaf sets develop. This leaf complexity continues to increase into the later vegetative stages, under ideal environmental conditions. A considerably higher level of tolerance of extreme environmental pressures (temperatures, light, pests, and pathogens) has been observed.

Plants of the new variety, FS-tp2', differ from plants of the seed parent 'Pineapple Express' primarily in terms of having Type 2 leaf morphology. Plants of the new variety, FS-tp2, differ from plants of the pollen parent 'Holy Banana' primarily in terms of having Type 2 leaf morphology.

Some embodiments of the invention relate to a seed from a *Cannabis* plant designated 'FS-tp2' wherein a representative sample of seed of said plant has been deposited under NCIMB No. 43854.

Some embodiments of the invention relate to a *Cannabis* plant, or plant part, tissue, or cell thereof produced by growing the seed of 'FS-tp2', or a descendant thereof. Plant parts can include the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like.

The plants, or plant parts of the invention display Type 2 leaf morphology, as defined herein.

Some embodiments of the invention relate to uses and methods of the plant in a breeding program to produce *cannabis* progeny comprising at least one characteristic of Type-2 morphology and genetic capacity to produce Type-2 leaf morphology in progeny. Details of existing *Cannabis* plants varieties and breeding are described in Potter et al. (2011, World Wide Weed: Global Trends in *Cannabis* Cultivation and Its Control), Holland (2010, The Pot Book: A Complete Guide to *Cannabis*, Inner Traditions/Bear & Co, ISBN1594778981, 9781594 778988), Green I (2009, The *Cannabis* Grow Bible: The Definitive Guide to Growing Marijuana for Recreational and Medical Use, Green Candy Press, 2009, ISBN 1931160589, 9781931160582), Green II (2005, The *Cannabis* Breeder's Bible: The Definitive Guide to Marijuana Genetics, *Cannabis* Botany and Creating Strains for the Seed Market, Green Candy Press, 1931160279, 9781931160278), Starks (1990, Marijuana Chemistry Genetics, Processing & Potency, ISBN 0914171399, 9780914171393), Clarke (1981, Marijuana Botany, an Advanced Study: The Propagation and Breeding of Distinctive *Cannabis*, Ronin Publishing, ISBN 091417178X, 9780914171782), Short (2004, Cultivating Exceptional *Cannabis*: An Expert Breeder Shares His Secrets, ISBN 1936807122, 9781936807123), Cervantes (2004, Marijuana Horticulture: The Indoor/Outdoor Medical Grower's Bible, Van Patten Publishing, ISBN 187882323X, 9781878823236), Franck et al. (1990, Marijuana Grower's Guide, Red Eye Press, ISBN 0929349016, 9780929349015), Grotenhermen and Russo (2002, *Cannabis* and Cannabinoids: Pharmacology, Toxicology, and Therapeutic Potential, Psychology Press, ISBN 0789015080, 9780789015082), Rosenthal (2007, The Big Book of Buds: More Marijuana Varieties from the World's Great Seed Breeders, ISBN 1936807068, 9781936807062), Clarke, R C (*Cannabis*: Evolution and Ethnobotany 2013), King, J (Cannabible Vols 1-3, 2001-2006), and four volumes of Rosenthal's Big Book of Buds series (2001, 2004, 2007, and 2011), each of which is herein incorporated by reference in its entirety for all purposes.

The present invention also relates to variants, mutants and trivial modifications of the seeds, plant parts and/or whole plants of the *Cannabis* plants of the present invention. Variants, mutants and trivial modifications of the seeds, plants, plant parts, plant cells of the present invention can be generated by methods well known and available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knock-outs/knock-ins, antisense and RNA interference. For more information of mutagenesis in plants, such as agents, protocols, see Acquaah et al. (Principles of plant genetics and breeding, Wiley-Blackwell, 2007, ISBN 1405136464, 9781405136464,) which is herein incorporated by reference in its entirety.

The present invention also relates to a mutagenized population of the *Cannabis* plants of the present invention, and methods of using such populations. In some embodiments, the mutagenized population can be used in screening for new *Cannabis* lines which comprises one or more or all of the morphological, physiological, biological, and/or chemical characteristics of *Cannabis* plants of the present invention.

In some embodiments, the new *Cannabis* plants obtained from the screening process comprise one or more or all of the morphological, physiological, biological, and/or chemical characteristics of *Cannabis* plants of the present invention, and one or more additional or different new morphological, physiological, biological, and/or chemical characteristic.

The present invention also provides any compositions or any products made from or isolated from the plants of the present invention. In some embodiments, the compositions/products comprises extract of the plants. In some embodiments, the extract contains higher percentage of terpenes/terpenoids compared to extract isolated from a control *Cannabis* plant variety (e.g., an existing variety, such as a recreational *Cannabis* plant variety). In some embodiments, the invention relates to a smokable or edible product comprising the *Cannabis* plant, or plant part, tissue, or cell.

The present invention provides methods of using the *Cannabis* plants or any parts, any compositions, or any chemicals derived from said plants of the present invention.

In some embodiments, the plants of the present invention can be used to produce new plant varieties. In some embodiments, the plants are used to develop new varieties or hybrids with desired phenotypes.

In some embodiments, selection methods, e.g., molecular marker assisted selection, can be combined with breeding methods to accelerate the process. Additional breeding methods known to those of ordinary skill in the art, e.g., methods discussed in Chahal and Gosal (Principles and procedures of plant breeding: biotechnological and conventional approaches, CRC Press, 2002, ISBN 084931321X, 9780849313219), Taji et al. (In vitro plant breeding, Routledge, 2002, ISBN 156022908X, 9781560229087), Richards (Plant breeding systems, Taylor & Francis US, 1997, ISBN 0412574500, 9780412574504), Hayes (Methods of Plant Breeding, Publisher: READ BOOKS, 2007, ISBN1406737062, 9781406737066), each of which is incorporated by reference in its entirety. The Cannabis genome has been sequenced (Bakel et al., The draft genome and transcriptome of Cannabis sativa, Genome Biology, 12(1 0):R102, 2011). Molecular makers for Cannabis plants are described in Datwyler et al. (Genetic variation in hemp and marijuana (Cannabis sativa L.) according to amplified fragment length polymorphisms, J Forensic Sci. 2006 March; 51(2):371-5.), Pinarkara et al., (RAPD analysis of seized marijuana (Cannabis sativa L.) in Turkey, Electronic Journal of Biotechnology, 12(1), 2009), Hakki et al., (Inter simple sequence repeats separate efficiently hemp from marijuana (Cannabis sativa L.), Electronic Journal of Biotechnology, 10(4), 2007), Datwyler et al., (Genetic Variation in Hemp and Marijuana (Cannabis sativa L.) According to Amplified Fragment Length Polymorphisms, J Forensic Sci, March 2006, 51(2):371-375), Gilmore et al. (Isolation of microsatellite markers in Cannabis sativa L. (marijuana), Molecular Ecology Notes, 3(1): 105-107, March 2003), Pacifico et al., (Genetics and marker assisted selection of chemotype in Cannabis sativa L.), Molecular Breeding (2006) 17:257-268), and Mendoza et al., (Genetic individualization of Cannabis sativa by a short tandem repeat multiplex system, Anal Bioanal Chem (2009) 393:719-726), each of which is herein incorporated by reference in its entirety.

In some embodiments, the Cannabis plant, or plant part, tissue, or cell of 'FS-tp2' comprises at least one of a cannabinoid profile and a terpene profile as set forth in Tables 1 and 2, respectively.

TABLE 1

Representative profile of certain cannabinoids as determined by liquid chromatography (percent dry weight of flower).

| Cannabinoid | Percent | Percent | Percent |
| --- | --- | --- | --- |
| d9-THC | 0.44 | 0.55 | 0.66 |
| THCA | 12.66 | 15.83 | 19 |
| THCVA | 0.1 | 0.13 | 0.156 |
| CBGA | 0.38 | 0.47 | 0.56 |
| Total | 13.62 | 17.03 | 20.44 |
| Total THC | 11.54 | 14.43 | 17.32 |

TABLE 2

Representative profile of certain terpenes (percent dry weight of flower).

| Terpene | Percent | Percent | Percent |
| --- | --- | --- | --- |
| a-Pinene | 0.15 | 0.30 .15 | 0.45 |
| Camphene | 0.005 | 0.01 .005 | 0.015 |
| b-Myrcene | 0.39 | 0.78 .39 | 1.17 |
| b-Pinene | 0.05 | 0.10 | 0.15 |
| d-Limonene | 0.03 | 0.06 | 0.09 |
| b-Ocimene | 0.045 | 0.09 | 0.135 |
| Linalool | 0.015 | 0.03 | 0.045 |
| Geraniol | 0.005 | 0.01 | 0.015 |
| b-Caryophyllene | 0.04 | 0.08 | 0.12 |
| a-Caryophyllene | 0.03 | 0.06 | 0.09 |
| trans-Nerolidol | 0.025 | 0.05 | 0.075 |
| Total Terpenes | 0.8 | 1.6 | 2.4 |

In some embodiments, the invention relate to a Cannabis clone regenerated from the Cannabis plant of descended from the plant, or plant part, tissue, cell or seed of 'FS-tp2' wherein the plant is a clonal descendent.

In some embodiments, the invention relates to a method of producing an F1 Cannabis seed, wherein the method includes crossing the plant with a different Cannabis plant, and harvesting the resultant F1 cannabis seed. In some embodiments, the invention relates to the F1hybrid cannabis seed produced by this method. In some embodiments, the invention relates to a F1 hybrid Cannabis plant produced by growing the F1 hybrid cannabis seed. In some embodiments, the invention relates to a cannabis clone regenerated from the F1 hybrid Cannabis plant. In some embodiments, the invention relates to a smokable or edible product comprising cannabis tissue from the F1 hybrid Cannabis plant.

The following detailed description sets forth distinctive characteristics of 'FS-tp2'. The data which define these characteristics was collected from asexual reproductions of the original selection. Dimensions, sizes, colors, and other characteristics are approximations and averages set forth as accurately as possible. The plant history was taken on plants before flowering, at approximately 120 days of age, and the descriptions relate to plants grown in Madera County, Calif., U.S.A. Color notations are in reference to the standard hexadecimal Web Pantone Color Chart known to those of ordinary skill in Internet web site design.

Applicant is prepared to make a deposit of seeds or plant tissue in the even that claims are submitted reciting such a deposit of seeds or plant tissue.

Type: Herbaceous tap-rooted annual

Classification: Cultivars of 'Cannabis sativa', possessing traits of the subspecies, 'C. sativa ssp indica (Lamarck)'. When navigating the key of Small and Cronquist, ID., the first couplet separates individuals based on their ability to intoxicate. This cultivated line possesses intoxicating properties, and so the subspecies sativa and its varieties (var. sativa and spontanea) are eliminated from consideration. Within the next couplet distinguishing within the subspecies indica, fruits are required to separate between the varieties (var. indica and var kafiristanica). No fruits were found on any of the individuals observed, and so discrimination between the varieties is impossible with this key. As the parents of the variety FS-tp2 were either of C. sativa ssp. sativa or a C. sativa ssp. sativa hybrid with C. sativa ssp. indica by this taxonomic approach we can assume that FS-tp2 is a C. sativa hybrid of predominantly C. sativa ssp. sativa heritage.

a. Family—Cannabaeae.
    b. Genus—Cannabis.
    c. Species—sativa
    d. Common Name—marijuana Parentage: Female Parent—C. sativa ssp. sativa 'Pineapple Express' Male Parent C. sativa hybrid 'Holy Banana'

Market Class: A medicinal herb intended for use as medical oil, and medicinal herb for sale in cannabis dispensaries and as a home garden plant for ornamental, medicinal, and/or recreational use.

PLANT

General:
    a. Origin—Madera County, Calif., U.S.A.
    b. Parentage—Female Parent—C. sativa ssp. sativa 'Pineapple Express'.
    c. Male Parent—C. sativa hybrid 'Holy Banana'.
    d. Growth habit—Upright and determinate.
    e. Height—Approximately 200 cm with additional growth as plant matures.
    f. Plant Spread—Approximately 120 cm and depends on pruning techniques.

g. Growth Rate—Growth rate and flowering is dependent on both short days and environment. Typical growth has been recorded between 120 and 65 days depending on planting time.
h. Branching Characteristics—Racemose, with monopodial branching in vegetative state and sympodial when the plant becomes reproductive.
i. Length of Primary Lateral Branches—Branch length changes with placement on plant. Lower, longer branches are approximately 100 cm.
j. Quantity of Primary Lateral Branches—At least one primary branch emerges from each internode with an average of at least 20 branches.
k. Characteristics of Primary Lateral Branches:
    a. Color—Pale green similar to # d8cb73, with streaks of purple gray anthocyanin similar to #282725.
    b. Texture—Smooth
    c. Strength—Strong, rigid.
l. Internode length: Approximately 5-15 cm in late vegetative cycle but varies depending on environment and age of plant, can be up to approximately 20 cm or more.
m. Cold hardiness—Has not been grown in all environments including harsh winter environments.
n. Cold tolerance—Cold tolerance is expected to be low.
o. Chilling requirement—Has not been grown in all environments and is typically grown in a single environment from selectively pollinated seeds. FS-tp2 is classed as 'low chill'.
p. Shipping tolerance—Not available. This plant has never been shipped.

FOLIAGE

General: Complex leaves with approximately 4-12 palmate veins. Large number of bipinnate leaflets with occasional deep hooks on smooth. Leaves alternate.
    a. Leaf—Foliage occurs at each internode on the main stem, primary and secondary branches. The data refer to a mature leaf on a late vegetative plant.
    b. Arrangement—Alternate.
    c. Quantity—Mature plants can possess over hundreds of leaves.
    d. Leaf color (Top side)—Ranges from a bright green #5d8c1f to a dark purple gray #282725 when planted outside. Leaves near the flowering top of the plant can be white in appearance due to trichome density.
    e. Leaf color (Under side)—Matte, a light green similar to # d8cb73.
    f. Leaf arrangement—Alternate.
    g. Leaf shape—Compound palmate bipinnate.
    h. Leaf margins—Leaflets have smooth margins.
    i. Undulation of margin—Margin is smooth/undulate with the exception of a few serrate hooks on leaflets near the apex of each tip.
    j. Leaf apices—Acuminate.
    k. Leaf bases—Hastate.
    l. Leaf width—Varies from approximately 12 to 20 cm depending on age of leaf.
    m. Leaf length—Varies from approximately 12 to 20 cm depending on age of leaf.
    n. Texture of top and bottom surfaces—Ranges from smooth to glandular on mature leaves near flowering tip.
    o. Appearance of top and bottom surfaces—Matte.
    p. Venation type—Palmate.
    q. Petiole length—Approximately 10 cm on a mature leaf, varies with plant age.
    r. Petiole color—Near # a7bf55.
    s. Petiole texture—Smooth.

Inflorescence

General:
a. Natural flowering season—Summer (July-October) Plant started from seed will flower approximately 8 weeks from planting, depending on planting date and daylength. Buds are compact and occur in groups, with approximately 100 flowers found in a 3 cm diameter bud.
b. Inflorescence and flower type and habit—The apical inflorescence type is a raceme and the flower type is dioecious, with sessile habit. The female flowers with tight, compact groups of flowers is composed of a bract wrapped around the ovary, with 2 stigmas emerging from the bract at maturity. The male flowers are compact groups composed of reduced tepals surrounding and 5 anthers until maturity.
c. Fragrance—Sweet and fruity, with notes of citrus (lemon, lime) as well as berry. Hints of pine.
d. Female flower and bud:
    i. Bud Shape—Accumate.
    ii. Bud Length—Approximately 1 cm.
    iii. Bud Diameter—Approximately 0.3 cm.
    iv. Bract Diameter—Approximately 0.3 cm.
    v. Bract Length—Approximately 1 cm.
    vi. Bract quantity per flower—1.
    vii. Bract Shape—Beaked.
    viii. Bract Base—Ovoid.
    ix. Bract Texture—Glandular.
    x. Stigma length—Approximately 0.5 cm, extending from bract.
    xi. Stigma color—White.
    xii. Stigma number—2 per flower.
    xiii. Stigma shape—Acicular with hairy surface.
    xiv. Ovary position—Inferior.
    xv. Ovary shape—Ovoid.
    xvi. Ovary length—Approximately 1 mm.
e. Male flower and bud: Tepals are rudimentary and only cover a small portion of the immature anthers. Anthers are held on short filaments difficult to be observed by the naked eye.
    i. Bud Shape—Acicular.
    ii. Bud Length—Approximately 1 cm.
    iii. Bud Diameter—Approximately 0.1 cm.
    iv. Tepal Length—Approximately 0.1 cm.
    v. Tepal number—5.
    vi. Anther number—5.
    vii. Anther length—Approximately 0.3 cm.

Seeds a. Shape—Ovoid.
b. Length—Approximately 5 mm.
c. Width—Approximately 4 mm.

DEPOSIT INFORMATION

A seed sample of this invention has been deposited with an International Depositary Authority as established under the Budapest Treaty according to 37 CFR 1.803(a)(1), at the National Collections of Industrial, Food and Marine Bacteria Ltd. (NCIMB) in Aberdeen Scotland under NCIMB No. 43854.

To satisfy the enablement requirements of 35 U.S.C. 112, and to certify that the deposit of the *Cannabis* varieties of the present invention meets the criteria set forth in 37 CFR 1.801-1.809 and Manual of Patent Examining Procedure (MPEP) 2402-2411. 05, Applicant(s) hereby makes the following statements regarding the deposited *cannabis* variety: If the deposit is made under the terms of the Budapest Treaty, the instant invention will be irrevocably and without restriction released to the public upon the granting of a patent. If the deposit is made not under the terms of the Budapest Treaty, Applicant(s) provides assurance of compliance by the following statements:

1. During the pendency of this application, access to the invention will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 CFR 1.807; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon granting of any claims in this application, all restrictions on the availability to the public of the variety will be irrevocably and without restriction or condition removed by affording access to a deposit of the tissue sample of the same variety with the depository.

The various methods and techniques described above provide a number of ways to carry out the application. Of course, it is to be understood that not necessarily all objectives or advantages described are achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by including one, another, or several other features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, any numbers expressing quantities of ingredients, properties such as molecular weight, reaction conditions, and so forth, used to describe and claim certain embodiments of the disclosure are to be understood as being modified in some instances by the term "about." When "about" is used in the specification or in a claim, it refers to a number range, varying from the recited number in an amount that, taking into account the number itself and the quality of the characteristic to which the number refers, accounts for variability in measurement or performance that does not change the quality of the numerically-expressed characteristic. In the absence of information to the contrary, "about" can refer to the number plus or minus 0.1%, 0.5%, 1% or 5% of the number itself, as would be appreciated by a person of ordinary skill in the art in reference to the characteristic to which the number refers and the normal quantitative variability around that number that would be understood to not materially change that characteristic. Accordingly, in some embodiments, the numerical parameters set forth in the written description and any included claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are usually reported as precisely as practicable.

In some embodiments, the terms "a" and "an" and "the" and similar references used in the context of describing a particular embodiment of the application (especially in the context of certain claims) are construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Variations on preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A seed from *Cannabis* plant designated 'FS-tp2' wherein a representative sample of seed of said plant has been deposited under NCIMB No. 43854, wherein the plant displays Type 2 morphology, wherein the Type 2 morphology comprises a palmate leaf structure comprising 5-9 leaflets, each leaflet comprising 9 to 30 bipinnate lobes or secondary leaflets.

2. A Cannabis plant, or plant part, tissue, or cell thereof that is produced by growing a seed or clone from:
   a. a Cannabis plant designated 'FS-tp2' wherein a representative sample of seed of said plant has been deposited under NCIMB No. 43854; or
   b. a descendant of the *Cannabis* plant of claim 1 designated 'FS-tp2';
   wherein said plant grown from said seed or said clone displays Type 2 morphology, wherein the Type 2 morphology comprises a palmate leaf structure comprising 5-9 leaflets, each leaflet comprising 9 to 30 bipinnate lobes or secondary leaflets.

3. A method of breeding a progeny *Cannabis* plant, or plant part, tissue, or cell thereof, comprising growing a parent plant from a seed or clone from:
   a. a *Cannabis* plant designated 'TS-tp2' wherein a representative sample of seed of said plant has been deposited under NCIMB No. 43854; or
   b. a descendant of the *Cannabis* plant designated 'TS-tp2'; and
   providing the parent plant as at least one parent in a breeding program and selecting progeny displaying Type 2 morphology wherein the Type 2 morphology comprises a palmate leaf structure comprising 5-9 leaflets, each leaflet comprising 9 to 30 bipinnate lobes or secondary leaflets.

4. The Cannabis plant, or plant part, tissue, or cell of claim 2, wherein flower produced from said Cannabis plant, or plant part, tissue, or cell thereof comprises a cannabinoid profile of:
   a. total THC between 11.54% and 17.32%;
   b. THCVA between 0.1% and 0.156%;
   c. CBGA between 0.38% and 0.56%; and
   d. total cannabinoids between 13.62% and 20.44%; and a terpene profile of:
   a. a-Pinene between 0.15% and 0.45%;
   b. Camphene between 0.005% and 0.015%;
   c. b-Myrcene between 0.39% and 1.17%;
   d. b-Pinene between 0.05% and 0.15%;
   e. d-Limonene between 0.03% and 0.09%;
   f. b-Ocimene between 0.045% and 0.135%;
   g. Linalool between 0.015% and 0.045%;
   h. Geraniol between 0.005% and 0.015%;
   i. b-Caryophyllene between 0.04% and 0.12%;
   j. a-Caryophyllene between 0.03% and 0.09%;
   k. trans-Nerolidol between 0.025% and 0.075%; and
   l. total Terpenes between 0.8% and 2.4%
   wherein the percent-value is wt. % by dry weight of said flower.

5. The *Cannabis* plant or plant part, tissue, or cell of claim 2, wherein said plant part is selected from the group consisting of: stems, trichomes, leaves, and flower buds.

6. A plant produced by a plant of claim 2 wherein the production is by clonal propagation.

7. The plant of claim 2, wherein the descendent is an F1, F2, F3, or F4.

8. The plant of claim 2, wherein the descendent is an F1 or an F2.

* * * * *